United States Patent [19]

Inoue et al.

[11] Patent Number: 4,495,356
[45] Date of Patent: Jan. 22, 1985

[54] 1,4-DIHYDROPYRIDINE COMPOUND

[75] Inventors: Yoichi Inoue, Omiya; Toshio Matsumoto, Ageo; Hirosuke Niwa, Kawaguchi; Kenichi Suzuki, Saitama; Yasuo Hoshide, Tokyo, all of Japan

[73] Assignees: Nikken Chemicals Co., Ltd.; Institute of Organic Synthesis Academy of Sciences Latvian SSR., both of Tokyo, Japan

[21] Appl. No.: 468,663

[22] Filed: Feb. 22, 1983

[30] Foreign Application Priority Data

Feb. 23, 1982 [JP] Japan .................................. 57-026790

[51] Int. Cl.³ .......................................... C07D 405/04
[52] U.S. Cl. .................... 546/268; 514/893
[58] Field of Search ........................................ 546/268

[56] References Cited

U.S. PATENT DOCUMENTS

| | | | |
|---|---|---|---|
| 3,485,847 | 12/1969 | Bossert et al. | 546/268 |
| 3,511,847 | 5/1970 | Loev et al. | 546/268 |
| 3,647,807 | 3/1972 | Bossert et al. | 546/268 |
| 3,773,773 | 11/1973 | Bossert | 546/268 |
| 3,905,970 | 9/1975 | Bossert et al. | 546/268 |

FOREIGN PATENT DOCUMENTS 1426499  2/1976  United Kingdom .

OTHER PUBLICATIONS

Shoin et al., Clinical Evaluation of Medicine, pp. 89-91, 9-1982.
Blum et al., The Lancet, 12-1977, p. 1153.
Beeson et al., Textbook of Medicine, p. 1645.
Krupp et al., Current Diagonis Treatment, 1975, p. 369.
Medical Dictionary 21st Edition.
Perrissoud et al., Naunyn–Schmiedeberg's Arch. Pharmacol. 312, 285-291, 1980.
Imaizumi et al., Japan J. Pharmacol. 31, 15-21, 1981.
Latvijas PSR Zinatnu Akademijas Vestis No. 7, 107-112, 1972.
Thijin Shokan, General Discussion for Development of Medicine, p. 99, 1970.

Primary Examiner—Jane T. Fan
Attorney, Agent, or Firm—Handal & Morofsky

[57] ABSTRACT 1,4-Dihydropyridine compound having the general formula:

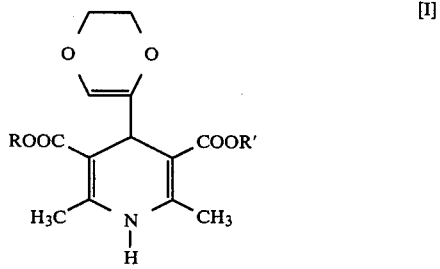

wherein R and R' are independently a methyl, ethyl, or propyl group. This compound has a remarkable liver protective action and a low toxicity.

4 Claims, No Drawings

1,4-DIHYDROPYRIDINE COMPOUND

The present invention relates to a novel 1,4-dihydropyridine compound and a method for the preparation thereof. More specifically, the present invention relates to a novel 1,4-dihydropyridine compound having the general formula:

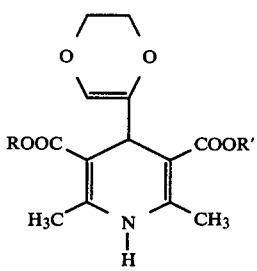

wherein R and R' are independently a methyl, ethyl or n-propyl group and a method for the preparation thereof.

The 1,4-dihydropyridine compounds having the above-mentioned general formula [I] are novel compounds which have not been reported in any literatures. These compounds have a remarkable liver protective action and a low toxicity as mentioned hereinbelow. Accordingly, these compounds are useful as medicine for treatment of hepatic disease.

The 1,4-dihydropyridine compounds having the above-mentioned general formula [I] can be prepared by reacting 2-formyl-p-dioxene having the formula [II], with acetoacetic acid lower alkyl ester having the general formula [III], wherein R is the same as defined above and β-aminocrotonic acid lower alkyl ester having the general formula [IV] wherein R' is the same as difined above in the presence of, or in the absence of, an organic solvent such as ethanol, n-propanol, isopropanol and pyridine. These reactions per se are essentially known in the preparation of conventional 1,4-dihydropyridine compounds. The reaction proceeds as follows:

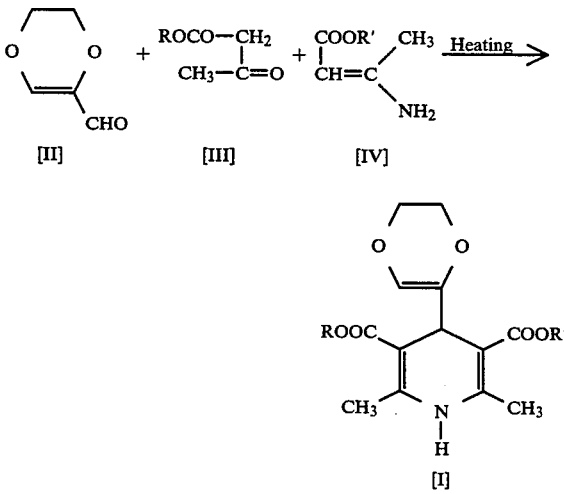

The above-mentioned compounds [I] can also be prepared, by the known reactions set forth in, for example, Japanese Examined Patent Publication (Kokoku) Nos. 46-40625, 48-6470 and 56-37225.

The above-mentioned starting compounds [II], [III] and [IV] in the above-mentioned reaction are of known compounds which are readily purchased, or can be readily prepared by those skilled in the art. For instance, the acetoacetic acid lower alkyl esters and the β-aminocrotonic acid lower alkyl esters are those which are conventionally used as a starting compound for the production of 1,4-dihydropyridine compounds and which are commercially available on the market. The 2-formyl-p-dioxene can be prepared from p-dioxene via 2-ethoxy-3-diethoxymethyl-p-dioxane according to a method described in, for example, M. S. Shostakovskii, Izvest. Akad. Nauk. S.S.S.R. Otdel. Khim. Nauk., 1685, (1961).

The 1,4-dihydropyridine compounds [I] formed in the above-mentioned reaction can be separated from the reaction mixture and can be purified in any conventional techniques including a solvent extraction, a chromatographic separation, crystallization from an appropriate solvent such as isopropanol and n-hexane-ethyl acetate.

The above-mentioned reaction can be carried out at a temperature of, for example, 50° C. to 200° C., desirably 70° C. to 160° C. Although there is no limitation in the mole ratio of the starting compounds [II], [III] and [IV], these compounds can be desirably used in an approximate equimolar amount.

As is clear from the results shown in Examples below, the present compounds are effective for the prevention and treatment of hepatic disorders and also have a low toxicity. Accordingly, it is clear that the present compounds are a medicine for treatment of hepatic disease caused by various factors.

The present invention will be further illustrated by, but is by no means limited to, the following examples illustrating the synthesis of the present compounds [I] as well as the pharmacological test data for the evaluation thereof.

EXAMPLE 1 (SYNTHESIS EXAMPLE)

Synthesis of 3,5-diethoxycarbonyl-4-[2'-(5',6'-dihydro-p-dioxinyl)]-2,6-dimethyl-1,4-dihydropyridine.

A 1.14 g (0.01 mole) amount of 2-formyl-p-dioxene, 1.30 g (0.01 mole) of ethyl acetoacetate and 1.30 g (0.01 mole) of ethyl β-aminocrotonate were mixed in a flask and, then, the resultant mixture was stirred at a temperature of 160° C. for 6 hours. Thereafter, the reaction mixture was cooled to room temperature. The reaction mixture thus obtained was subjected to chromatographic purification by using a column packed with 160 g of silica gel. A mixed solvent of benzene and ethyl acetate (5:1) (V/V) was used as an eluent. The compound thus purified was recrystallized from isopropanol to obtain 1.27 g of the desired product. The yield was 37.6%.

The analytical data of this product were as follows:
m.p.: 150.0° to 151.0° C.

IR$\nu_{max}^{KBr}$ cm$^{-1}$: 3350 (NH), 1700 (C=O), 1640 (C=C), 1210 (C—O).

NMR ppm [δ] (CDCl$_3$, TMS): 1.30 (6H,t, 2×CH$_2$—CH$_3$), 2.31 (6H,s, 2,6-CH$_3$), 3.93 (4H,s, O—CH$_2$—CH$_2$—O), 4.19 (4H,q, 2×CH$_2$—CH$_3$), 4.48 (1H, S, 4-H), 5.87 (1H, S, vinyl-H), 6.25 (1H,br.NH).

Elementary analysis data (for C$_{17}$H$_{23}$NO$_6$): Calculated: C, 60.52; H, 6.87; N, 4.15 (%). Found: C, 60.79; H, 7.03; N, 4.03 (%).

EXAMPLE 2 (SYNTHESIS EXAMPLE)

Synthesis of 3,5-di-n-propyloxycarbonyl-4-[2'-(5',6'-dihydro-p-dioxynyl)]-2,6-dimethyl-1,4-dihydropyridine.

A 1.69 g (14.8 mmole) amount of 2-formyl-p-dioxane, 2.16 g (15.0 mmole) of n-propyl acetoacetate and 2.15 g (15.0 mmole) of n-propyl β-aminocrotonate were mixed in a flask and, then, the resultant mixture was stirred at a temperature of 130° C. to 140° C. for 6 hours. Thereafter, the reaction mixture was cooled to room temperature. The reaction mixture thus obtained was subjected to chromatographic purification by using a column packed with 160 g of silica gel. A mixed solvent of benzene and ethyl acetate (3:1) (V/V) was used as an eluent. The compound thus purified was recrystallized from isopropanol to obtain 1.30 g of the desired product. The yield was 24.0%.

The analytical data of this product were as follows:
m.p.: 117.5° to 118.5° C.
IR$\nu_{max}^{KBr}$ cm$^{-1}$: 3320 (NH), 1695 (C=O), 1650, 1620 (C=O, C=O), 1270 (C—O).
NMR ppm [δ] (CDCl$_3$, TMS): 0.98 (6H,t, 2×CH—$_2$CH$_3$), 1.70 (4H,m, 2×CH—$_2$CH$_2$—CH$_3$), 2.30 (6H,s, $\overline{2}$6-CH$_3$), 3.90 (4H,s, O—CH$_2$—CH$_2$—O), 4.08 (4H,t, 2XCOOCH$_2$—CH$_2$), 4.49 (1$\overline{H}$, s, 4-$\overline{H}$), 5.85 (1H,s, vinyl-H), 6.33 ($\overline{1H}$, br.NH).

Elementary analysis data (for C$_{19}$H$_{27}$NO$_6$): Calculated: C, 62.45; H, 7.45; N, 3.83 (%). Found: C, 62.34; H, 7.50; N, 3.81 (%).

EXAMPLE 3 (SYNTHESIS EXAMPLE)

Synthesis of 3,5-dimethoxycarbonyl-4-2'-(5',6'-dihydro-p-dioxinyl)-2,6-dimethyl-1,4-dihydropyridine.

A 1.72 g (0.015 mole) amount of 2-formyl-p-dioxene, 1.73 g (0.015 mole) of methyl acetoacetate and 1.72 g (0.015 mole) of methyl β-aminocrotanate were mixed in a flask and, then, the resultant mixture was stirred at a temperature of 145° C. for 3.5 hours. Thereafter, the reaction mixture was cooled to a room temperature. The reaction mixture thus obtained was subjected to chromatographic purification by using a column packed with 100 g of silica gel. A mixed solvent of benzene and ethyl acetate (4:1) (V/V) was used as an eluent. The compound thus purified was recrystallized from isopropanol to obtain 1.37 g of the desired product. The yield was 29.4%.

The analytical data of this product were as follows:
m.p.: 195.5° to 197.0° C.
IR$\nu_{max}^{KBr}$ cm$^{-1}$: 3320 (NH), 1700 (C=O), 1640 (C=O), 1210 (C—O).
NMR ppm [δ] (CDCl$_3$, TMS): 2.30 (6H,s, 2,6-CH$_3$), 3.72 (6H,s, 2XCH$_3$), 3.93 (4H, s, O—CH$_2$—CH$_2$—O), 4.43 (1H,s, 4-H), 5.86 (1H,s, vinyl-H), 6.10 (1H,br.NH).

Elementary analysis data (for C$_{15}$H$_{19}$NO$_6$): Calculated: C, 58.25; H, 6.19; N, 4.53 (%). Found: C, 58.33; H, 5.91; N, 4.46 (%).

EXAMPLE 4 (EVALUATION EXAMPLE)

Effect of 3,5-diethoxycarbonyl-4-[2'-(5',6'-dihydro-p-dioxinyl)]-2,6-dimethyl-1,4-dihydropyridine (compound of Example 1) on liver disorder induced by D-galactosamine.

The effect of the sample compound to be tested on hepatic disorder was evaluated by determining the levels of GOT, GPT and bilirubin, which are known as an indicator of hepatic disorder, in serum, after administering D-galactosamine hydrochloride and the sample compound to Wistar-Imamichi male rats (8 week age and body weight of 260 to 280 g) as follows.

Five rats were used in each test group. The sample compound (i.e., the compound prepared in Example 1) was suspended at a concentration of 40 mg/ml in a 0.1% aqueous solution of Tween-80 (Trademark of surfactant available from Atlas Chemical Corp.). Alpha-tocopherol was dissolved at a concentration of 40 mg/ml in olive oil. This solution was administered orally at a dose of 200 mg/kg each for 2 days (25 and 1 hours before the administration of D-galactosamine). D-galactosamine was dissolved at a concentration of 100 mg/ml in a Physiological saline and this solution was administered intraperitoneally at a single dose of 400 mg/kg one hour after the final administration of the sample compound.

Blood samples were collected from the carotid artery under pentobarbital anesthesia, 24 hours after the administration of D-galactosamine. The rats were fasted for 18 to 20 hours before collecting of blood sample.

The determination of GOT and GPT in serum was carried out according to a UV method and the determination of bilirubin was carried out according to a diazo method. The results are shown in Table 1.

TABLE 1

|  | Control (normal) | D-galactosamine administration groups | | |
|---|---|---|---|---|
|  |  | No combination compound | Combined with alpha-tocopherol | Combined with compound of Example 1 |
| GOT (KU) | 97 ± 3 | 6170 ± 1507 | 3065 ± 440 | 2194 ± 777 |
| GPT (KU) | 15 ± 1 | 2195 ± 460 | 1043 ± 189 | 862 ± 373 |
| Bilirubin (mg/dl) | 0.12 ± 0.02 | 0.43 ± 0.06 | 0.26 ± 0.02 | 0.30 ± 0.06 |

EXAMPLE 5 (EVALUATION EXAMPLE)

Effect of 3,5-diethoxycarbonyl-4-[2'-(5',6'-dihydro-p-dioxiynyl)]-2,6-dimethyl-1,4-dihydropyridine (compound of Example 1) on hepatic disorder induced by carbon tetrachloride.

The effect of the sample compound to be tested on hepatic disorder was evaluated by determining the levels of GOT, GPT, and bilirubin, which are known as an indicator of hepatic disorder, in serum, after administering carbon tetrachloride and the sample compound to SLC-Wistar male rats (10 week age and body weight of 240 to 260 g) as follows.

Five rats were used in each test group. The sample compound (i.e., the compound prepared in Example 1) was suspended at a concentration of 40 mg/ml in a 0.1% aqueous solution of Tween-80. Alpha-tocopherol was dissolved at a concentration of 40 mg/ml in an olive oil. This solution was administered orally at a dose of 200 mg/kg each for 2 days. Glutathione was dissolved at a concentration of 100 mg/ml in a 0.1% aqueous solution of Tween-80. This solution was orally administered at a dose of 500 mg/kg for 2 days. Carbon tetrachloride was intraperitoneally administered as a 10% olive oil solution at a dose of 5 ml/kg (0.5 ml/kg in terms of CCl$_4$) one hour after the final administration of the sample compound.

Blood samples were collected from the carotid artery under pentobarbital anesthesia, 24 hours after the administration of carbon tetrachloride. The rats were fasted for 18 to 20 hours before collecting of blood sample.

The determination of GOT and GPT in serum was carried out according to a UV method and the determination of bilirubin was carried out according to a diazo method. The results are shown in Table 2.

TABLE 2

|  | Control (normal) | No combination compound | CCl₄ administration groups | | |
|---|---|---|---|---|---|
|  |  |  | Combined with alpha-tocopherol | Combined with glutathione | Combined with compound of Example 1 |
| GOT (KU) | 73 ± 5 | 18228 ± 2032 | 5662 ± 793 | 11272 ± 1904 | 1800 ± 321 |
| GPT (KU) | 32 ± 3 | 10606 ± 1952 | 5764 ± 1564 | 7722 ± 1170 | 1396 ± 290 |
| Bilirubin (mg/dl) | 0.12 ± 0.02 | 0.26 ± 0.02 | 0.18 ± 0.02 | 0.22 ± 0.02 | 0.14 ± 0.02 |

EXAMPLES 6 AND 7 (EVALUATION EXAMPLE)

Effects of 3,5-di-n-propyloxycarbonyl-4-[2'-(5',6'-dihydro-p-dioxinyl)]-2,6-dimethyl-1,4-dihydropyridine (compound of Example 2), and 3,5-dimethoxycarbonyl-4-[2'-(5',6'-dihydro-p-dioxinyl)]-2,6-dimethyl-1,4-dihydropyridine (compound of Example 3) on hepatic disorder induced by carbon tetrachloride.

The effects of the sample compounds on hepatic disorders were evaluated by determining the levels of GOT, GPT, and bilirubin hepatoc in serum, after administering carbon tetrachloride and the sample compound to SLC-Wistar male rats (10 week age and body weight of 240 to 270 g) as follows.

Five rats were used in each test group. The sample compounds (i.e., the compounds prepared in Examples 2 and 3) were suspended at a concentration of 40 mg/ml in a 0.1% aqueous solution of Tween-80. Alpha-tocopherol was dissolved at a concentration of 40 mg/ml in olive oil. This solution was administered orally at a dose of 200 mg/kg each for 2 days. Glutathione was dissolved at a concentration of 100 mg/ml in a 0.1% aqueous solution of Tween-80. This solution was orally administered at a dose of 500 mg/kg for 2 days. Carbon tetrachloride was intraperitoneally administered as a 10% olive oil solution at a dose of 5 ml/kg (0.5 ml/kg in terms of CCl₄) one hour after the final administration of each sample compound.

Blood sampels were collected from the carotid artery under pentobarbital anesthesia, 24 hours after the administration of carbon tetrachloride. The rats were fasted for 18 to 20 hours before collecting of a blood sample.

The determination of GOT and GPT in serum was carried out according to a UV method and the determination of bilirubin was carried out according to a diazo method. The results are shown in Table 3.

EXAMPLE 8 (EVALUATION EXAMPLE)

Acute toxicity of 3,5-diethoxycarbonyl-4-[2'-(5',6'-dihydro-p-dioxinyl)]-2,6-dimethyl-1,4-dihydropyridine (compound of Example 1), 3,5-di-n-propyloxycarbonyl-4-[2'-(5',6'-dihydro-p-dioxynyl)]-2,6-dimehyl-1,4-dihydropyridine (compound of Example 2), and 3,5-dimethoxycarbonyl-4-[2'-(5',6'-dihydro-p-dioxinyl)]-2,6-dimehyl-1,4-dihydropyridine (compound of Example 3).

LD₅₀ values of the above-mentioned compounds were determined by observing SLC-Wistar male rats (5 week age and a body weight of 120 to 130 g) for 3 days after orally administering the sample compounds to be tested. The results were as follows:

| Compounds | LD₅₀ |
|---|---|
| Example 1 | about 2.0 g/kg |
| Example 2 | 2.0 g/kg or more |
| Example 3 | 2.0 g/kg or more |

We claim:
1. 1,4-Dihydropyridine compound having the general formula:

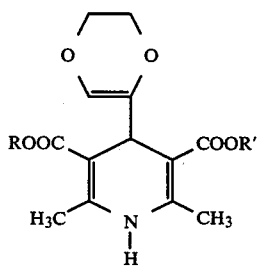

wherein R and R' are independently a methyl, ethyl, or n-propyl group.

2. 3,5-Diethoxycarbonyl-4-[2'-(5',6'-dihydro-p-dioxinyl)]-2,6-dimethyl-1,4-dihydropyridine according to claim 1.

3. 3,5-Di-n-propyloxycarbonyl-4-[2'-(5',6'-dihydro-p-dioxinyl)]-2,6-dimethyl-1,4-dihydropyridine according to claim 1.

4. 3,5-Dimethoxycarbonyl-4-[2'-(5',6'-dihydro-p-dioxinyl)]-2,6-dimethyl-1,4-dihydropyridine according to claim 1.

TABLE 3

|  | Control (normal) | No combination compound | CCl₄ administration groups | | |
|---|---|---|---|---|---|
|  |  |  | Combined with alpha-tocopherol | Combined with compound of Example 2 | Combined with compound of Example 3 |
| GOT (KU) | 97 ± 10 | 16650 ± 1636 | 14558 ± 1049 | 2456 ± 734 | 901 ± 127 |
| GPT (KU) | 46 ± 6 | 10266 ± 818 | 9106 ± 591 | 1443 ± 228 | 680 ± 107 |
| Bilirubin (mg/dl) | 0.10 ± 0.00 | 0.24 ± 0.02 | 0.26 ± 0.04 | 0.13 ± 0.03 | 0.14 ± 0.02 |